United States Patent [19]

Seshimoto

[11] Patent Number: 4,510,035
[45] Date of Patent: Apr. 9, 1985

[54] LIQUID TRANSPORTING AND DISTRIBUTING DEVICE AND IONIC ACTIVITY MEASURING DEVICE USING THE SAME

[75] Inventor: Osamu Seshimoto, Asaka, Japan

[73] Assignee: Fuji Photo Film Co., Ltd., Minami-ashigara, Japan

[21] Appl. No.: 466,961

[22] Filed: Feb. 16, 1983

[30] Foreign Application Priority Data

Feb. 16, 1982 [JP] Japan .................................. 57-23149

[51] Int. Cl.³ ............................................ G01N 27/28
[52] U.S. Cl. .................................... 204/411; 204/412; 204/416; 422/99; 422/100
[58] Field of Search ...................... 204/411, 412, 416; 422/50, 55, 56, 57, 58, 68, 99, 100

[56] References Cited

U.S. PATENT DOCUMENTS

| | | | |
|---|---|---|---|
| 3,783,696 | 1/1974 | Coleman | 73/425.4 |
| 4,254,083 | 3/1981 | Columbus | 422/55 |
| 4,269,803 | 5/1981 | Jessop | 422/63 |
| 4,271,119 | 6/1981 | Columbus | 422/50 |
| 4,299,919 | 11/1981 | Jellinek | 204/412 X |
| 4,323,536 | 4/1982 | Columbus | 422/56 |

Primary Examiner—G. L. Kaplan
Attorney, Agent, or Firm—Fleit, Jacobson, Cohn & Price

[57] ABSTRACT

A device for transporting and distributing a liquid comprising at least one internal liquid passage, a liquid introducing hole extending from the outer surface of the device to the liquid passage, and at least one liquid distribution opening extending from the liquid passage to the outer surface. The inlet of the liquid introducing hole is adapted to receive a port of a liquid injector in airtight relation therewith. At least one air discharging hole may extend from the liquid passage to the outer surface. An ionic activity measuring device is constructed by a combination of such devices. It comprises solid electrodes in contact with the liquid distribution openings and provided in a number equal to the number thereof, and at least one bridge extending between the liquid introducing holes, between the liquid passages or between the liquid distribution openings. The respective pairs of solid electrodes are able to selectively respond to a predetermined ion.

1 Claim, 11 Drawing Figures

LIQUID TRANSPORTING AND DISTRIBUTING DEVICE AND IONIC ACTIVITY MEASURING DEVICE USING THE SAME

BACKGROUND OF THE INVENTION

1. Field of the Invention

This invention relates to a device for transporting and distributing a liquid, and more particularly to an ionic activity measuring device which comprises the liquid transporting and distributing device and which is useful for potentiometric measurement of the concentration or ionic activity of an ion contained in liquid samples, such as water, body fluids (for example, whole blood, blood plasma, blood serum, urine and the like), and aqueous solutions (for example, wine, beer and the like).

2. Description of the Prior Art

Generally, from the clinical or industrial point of view, it is important to selectively measure the concentration or ionic activity of an inorganic ion, for example $K^\oplus$, $Na^\oplus$, $Ca^{2\oplus}$, $Cl^\ominus$, or $HCO_3^\ominus$, contained in body fluids or aqueous solutions. For this purpose, it has been proposed to use dry type, ion-selective electrodes, which are easy to store and operate, for measurement. As an example of the dry type, ion-selective electrode (half cell or single electrode), it has been proposed in Japanese Unexamined Patent Publication No. 52(1977)-142584 (corresponding to U.S. Pat. Nos. 4,053,381 and 4,214,968) to coat or laminate four functional layers on a substrate and form a film-like, dry type, solid ion selective electrode. (Hereinafter sometimes referred to as the solid electrode). To conduct measurement with the film-like, solid electrode of this type, a very small amount (e.g. between 5 $\mu l$ and 50 $\mu l$) of a liquid sample is applied to a predetermined position on the solid electrode.

FIG. 1 is a schematic perspective view showing a conventional film-like, solid, ion-selective electrode comprising four coated or laminated functional layers. In FIG. 1, a solid electrode 10 comprises a metal layer 11, a water-insoluble metal salt layer 12, a reference electrolyte layer 13 and an ion-selective layer 14 sequentially coated or laminated as the functional layers on a substrate 19. For example, the metal layer 11 is formed of silver, the water-insoluble metal salt layer 12 is formed of silver chloride, the reference electrolyte layer 13 is made by dispersing potassium chloride in a hydrophilic organic polymer binder, and the ion-selective layer 14 is an organic ion selective layer containing an organic compound capable of selectively responding to a predetermined ion, a carrier solvent and an organic polymer binder.

It has also been proposed in Japanese Unexamined Patent Publication No. 57(1982)-17851 to use a solid electrode comprisng three coated or laminated functional layers, in which the reference electrolyte layer 13 shown in FIG. 1 is omitted, and the ion-selective layer 14 consisting of organic materials is directly positioned on the water-insoluble metal salt layer 12. Further, Japanese Unexamined Patent Publication No. 48(1973)-82897 (U.S. Pat. No. 4,115,209) discloses a dry type, solid electrode comprising two coated or laminated functional layers, in which the water-insoluble metal salt layer 12 and the reference electrolyte layer 13 shown in FIG. 1 are omitted, and an ion-selective layer 14 containing an ion exchange material is positioned directly on the metal layer 11.

The ion-selective layer 14 is essential if the ion to be measured is $K^\oplus$, $Na^\oplus$, $Ca^{2\oplus}$ or $HCO_3^\ominus$. If the ion to be measured is $Cl^\ominus$ and the electrode comprises a metal layer 11 made of silver and an insoluble metal salt layer 12 made of silver chloride, it is possible to replace the ion-selective layer 14 with a protective layer made of, for example, cellulose acetate, polymethacrylic acid, polyacrylic acid, or poly(2-hydroxyethyl acrylate) employed in a halogen ion-permeable protective layer as disclosed in Japanese Unexamined Patent Publication No. 55(1980)-89741 (corresponding to U.S. Pat. Nos. 4,199,411 and 4,199,412).

When the ionic activity is determined by use of two solid electrodes described above, they are connected with each other by a bridge described later, and a potentiometer is connected therebetween. Then, a sample and a standard solution respectively are spotted onto the solid electrodes, and the difference in potential between the electrodes which is indicated on potentiometer is read to determine the activity of an ion contained in the sample solution. In this case, these solid electrodes must be electrically isolated from each other.

FIG. 2 is a schematic perspective view showing a conventional ionic activity measuring device comprising two film-like, solid electrodes of the type described above, as disclosed in FIGS. 4-5 of Japanese Unexamined Patent Publication No. 52(1977)-142584 (FIGS. 8-10 of U.S. Pat. No. 4,053,381). In this conventional device, in order to electrically isolate two solid electrodes 10 from each other, they are put in spaced relation to each other in a frame 30 made of a non-conductive material such as a plastic, and a bridge 201 defined by a groove coated with a surface active agent and having an open top side which extends between the electrodes 10. In FIG. 2, the bridge 201 defined by a groove is positioned between holes 28 and 29 at the respective solid electrodes 10.

FIG. 3 is a schematic perspective view showing another conventional ionic activity measuring device, as disclosed in Japanese Unexamined Patent Publication No. 55(1980)-20499 (U.S. Pat. No. 4,184,936). In FIG. 3, a hole 233 is formed in the upper surface of a flat member 31, and a bridge 20 provided with holes 28 and 29 are positioned in the hole 323, so that an ion can be transported between electrodes 10. The bridge 20 is of the type generally called the capillary bridge, which is used to promote ion transport between the electrodes 10.

FIG. 4 is a sectional view taken along the line S—S in FIG. 3. The capillary bridge 20 is formed of a three-layer laminate of various configurations. As shown in FIG. 4, the bridge 20 is constituted by three flat strips through which the holes 28 and 29 are perforated. Droplets of solutions 41 and 42 are applied to the holes 28 and 29, respectively. The capillary bridge 20 comprises a non-porous bottom substrate 22 existing nearest to the solid electrode, an intermediate porous layer 21, and a top non-porous hydrophobic layer 24 existing farthest from the solid electrode.

To prevent the functional layers of the electrodes 10 from being short-circuited at their edges due to the sample or the standard solution bleeding out of the bridge 20, the bridge 20 is sealed from the electrodes 10 at least at the circumferences of the holes 28 and 29.

The intermediate porous layer 21 is made, for example, of porous paper, a membrane filter, threads, a fabric or the like. The layer 21 absorbs the liquid droplets 41 and 42 and causes them to contact each other, resulting in ion transport. When liquid droplets are applied to the holes 28 and 29, the droplets fill up the holes, form a large "lid" on the top layer 24, and are then absorbed into the layer 21 in five to 30 seconds. The liquids diffuse through the bridge 20 and come into contact with each other at approximately equal distances from the holes 28 and 29, i.e., approximately at the center of the bridge 20. In this way, ion transport becomes possible, and a potential develops between the electrodes 10. Further, sufficient liquids to fill up the holes 28 and 29 are not absorbed into the layer 21 but remain in the holes 28 and 29.

Other examples of the materials preferable as the intermediate porous layer are described in Japanese Unexamined Patent Publication No. 52(1977)-142584.

Other examples of the bridge are described, for example, in Japanese Unexamined Patent Publication Nos. 55(1980)-59326 (U.S. Pat. Nos. 4,233,029 and 4,254,083) and 55(1980)-71942 (U.S. Pat. Nos. 4,217,119 and 4,302,313).

The ionic activity measuring device described above may be provided with many dry type, film-like electrodes having ion selective layers different from one another so as to measure activities of many different ions at the same time with one step of spotting the sample and the standard solution. However, studies conducted on this type of ionic activity measuring device revealed that it presents a very real problem as described below.

Namely, when the sample and the standard solution are applied to the holes of the bridge of the ionic activity measuring device provided with many electrodes, it is difficult for the liquids to be sufficiently distributed through the bridge and the respective electrodes by capillary action in a single liquid spotting step. Thus, it is difficult to measure the ionic activity in a stable manner. This problem is aggravated when the liquid has a high viscosity, as in the case of blood, and when the liquid transporting section involves a gap or an uneven level portion.

SUMMARY OF THE INVENTION

The primary object of the present invention is to provide a liquid transporting and distributing device which can transport and distribute a liquid even when it is usually difficult for the liquid to be transported and distributed by capillary action.

Another object of the present invention is to provide an ionic activity measuring device comprising the liquid transporting and distributing device.

The specific object of the present invention is to provide an ionic activity measuring device which can sufficiently distribute a sample and a standard solution through a bridge and electrodes by a single liquid spotting step, and which can stably measure ionic activity.

The liquid transporting-and-distributing device in accordance with the present invention comprises an outer surface, a hollow liquid passage positioned in the interior, a liquid introducing hole extending from said outer surface to said hollow liquid passage, and at least one liquid distribution opening extending from said hollow liquid passage to said outer surface, wherein the section of said liquid introducing hole intersecting with said outer surface or the vicinity of said section is adapted to receive or fit with a liquid supply port of a liquid introducing means in airtight relation therewith for liquid injection into said liquid introducing hole.

The device in accordance with the present invention can certainly and easily transport and distribute a liquid by use of an injecting means even when it is usually impossible to transport and distribute a liquid by capillary action because of a gap or an uneven level portion existing at the liquid transport section or because of a high viscosity of the liquid.

Further, the present invention provides an ionic activity measuring device comprising:

(a) a liquid transporting-and-distributing device comprising an outer surface, at least two independent hollow liquid passages positioned in the interior, at least two independent liquid introducing holes which extend from said outer surface to each of said hollow liquid passages, liquid outlet openings extending from the respective hollow liquid passages to said outer surface, at least one liquid outlet opening being provided per said hollow liquid passage, and air discharging holes extending from respective hollow liquid passages to said outer surface, at least one air discharging hole being provided per said hollow liquid passage, (b) solid electrodes which are in contact with said liquid outlet openings and which are provided in a number equal to the number of said liquid outlet openings, and (c) at least one bridge extending between said liquid introducing holes, between said hollow liquid passages, or between said liquid outlet openings, wherein the sections of said liquid introducing holes intersecting with said outer surface or the vicinities of said sections are adapted to receive or fit with a liquid supply port of a liquid introducing means in airtight relation therewith for liquid injection into said liquid introducing holes.

Even when the ionic activity measuring device in accordance with the present invention is provided with many electrodes, it can easily and completely distribute a liquid to the bridge and to the electrodes, and can stably measure the ionic activity. Further, the present invention is advantageous in that, even when the liquid has a high viscosity or the hollow liquid passages have an intermediate opening or the like and an uneven sectional geometry, liquid distribution can be conducted certainly with good reproducibility, by a single liquid spotting step, and it is possible to obtain highly reliable ionic activity data. Furthermore, the present invention makes it possible to shorten the length of the bridge as desired and to change the shape of the ionic activity measuring device.

In the present invention. the solid electrodes may have the same construction at those generally called half cells or single electrodes.

The present invention will hereinbelow be described in further detail with reference to the accompanying drawings.

DESCRIPTION OF THE PREFERRED EMBODIMENTS

Figure 1:
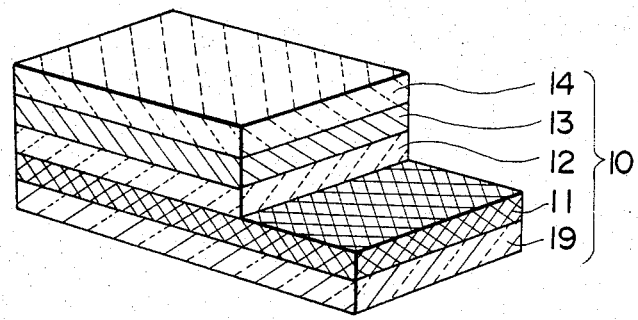
FIG. 1 is a schematic perspective view showing a conventional film-like solid ion-selective electrode comprising four coated or laminated functional layers.
Figure 2:
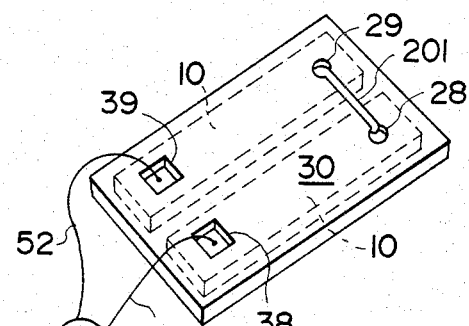
FIG. 2 is a schematic perspective view showing a conventional ionic activity measuring device comprising two film-like solid electrodes.
Figure 3:
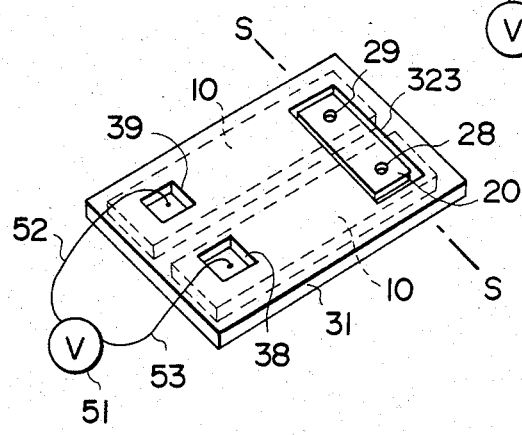
FIG. 3 is a schematic perspective view showing another conventional ionic activity measuring device.
Figure 4:
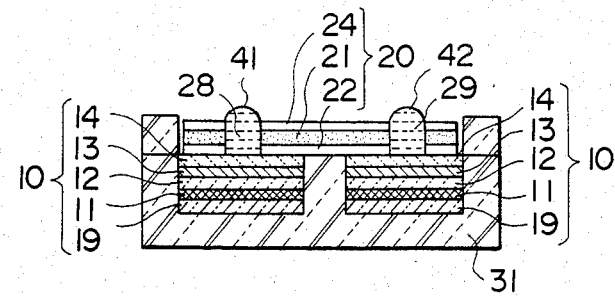
FIG. 4 is a sectional view taken along the line S—S in FIG. 3.

Preferred embodiments of the present invention will now be described with reference to FIGS. 5 to 11, wherein like reference numerals designate like or corresponding parts throughout.

Figure 5:
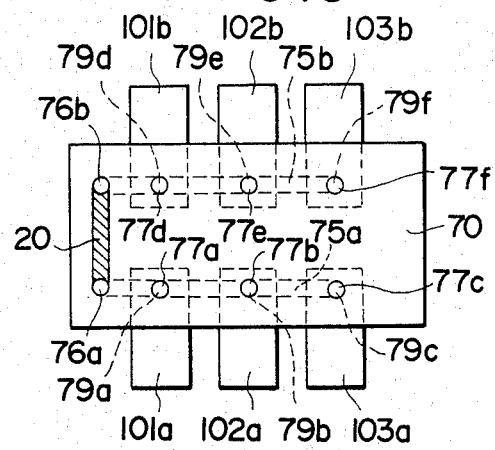
FIG. 5 is a plan view showing an embodiment of the ionic activity measuring device in accordance with the present invention.
Figure 6:
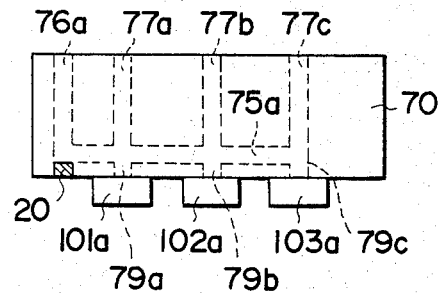
FIG. 6 is a side view of the embodiment shown in FIG. 5.

Referring to FIGS. 5 and 6 showing an embodiment of the ionic activity measuring device in accordance with the present invention, film-like, solid electrodes (ion-selective electrodes) 101a, 101b, 102a, 102b, 103a and 103b which may be of a known type are secured to the bottom of a substrate 70. The film-like solid electrodes 101a and 101b, 102a and 102b, and 103a and 103b are respectively paired with each other. Each pair has a common ion-selective ability, so that activities of three different ions can be measured at the same time. A bridge 20, which may be of any known type, is positioned at the lower section of the substrate 70 near an end thereof. In the interior of the substrate 70 are provided hollow liquid passages or communication cavities 75a and 75b for respectively establishing communication among the electrodes 101a, 102a, 103a, and one end of the bridge 20, and among the electrodes 101b, 102b, 103b, and the other end of the bridge 20. The communication cavity 75a is connected to the electrodes 101a, 102a and 103a by liquid outlet openings 79a, 79b and 79c, respectively. The communication cavity 75b is connected to the electrodes 101b, 102b and 103b by liquid outlet openings 79d, 79e and 79f, respectively. Further, the communication cavity 75a is open to a liquid introducing hole 76a and air discharging holes 77a, 77b, 77c, and the communication cavity 75b is open to a liquid introducing hole 76b and air discharging holes 77d, 77e, 77f.

Figure 9:
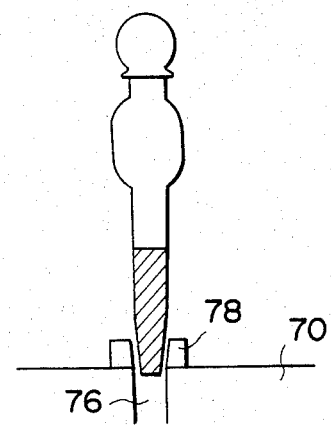
FIG. 9 is a schematic view showing the condition of liquid injection into the ionic activity measuring device in accordance with the present invention.

To measure ionic activities by use of the ionic activity measuring device shown in FIGS. 5 and 6, lead cables of potentiometers are connected between electrodes 101a and 101b, 102a and 102b, and 103a and 103b. Then, as shown in FIG. 9, liquid introducing means, for example, pipettes, are inserted into or fitted to the liquid introducing holes 76a and 76b in airtight relation thereto. In this way, a standard solution and a sample solution are injected into the communication cavities 75a and 75b, respectively, and distributed through the bridge 20 to the electrodes 101a, 102a, 103a, and the electrodes 101b, 102b, 103b. At this time, since there are the air discharging holes 77a, 77b, 77c, 77d, 77e and 77f and no high pressure develops on the bridge side, the standard solution and the sample solution are sufficiently distributed to these electrodes. Accordingly, the ionic activities can be measured stably by use of the potentiometers, and the respective electrodes can work equivalently to one another.

In the embodiment shown in FIGS. 5 and 6, it is possible to omit the air discharging holes 77a, 77b, 77d and 77e, and form only the air discharging holes 77c and 77f. Further, the position of the bridge 20 is not limited to the bottom of the substrate 70 near an end thereof. Thus, the bridge 20 may be formed at any position insofar as the bridge 20 contacts the communication cavities 75a and 75b at the ends thereof and can effect ion transport. Further, it is effective to position grooves for guiding the liquids overflowing at the time of liquid injection between the air discharging holes 77a and 77b, 77b and 77c, 77d and 77e, 77e and 77f. To further distribute the standard solution and the sample solution with certainty, it is possible to form layers of a surface active agent on the surfaces of the communication cavities 75a and 75b working as the hollow liquid passages, and the liquid outlet openings 79a, 79b, 79c, 79d, 79e and 79f for connecting the communication cavities 75a and 75b to the respective electrodes.

Figure 7:
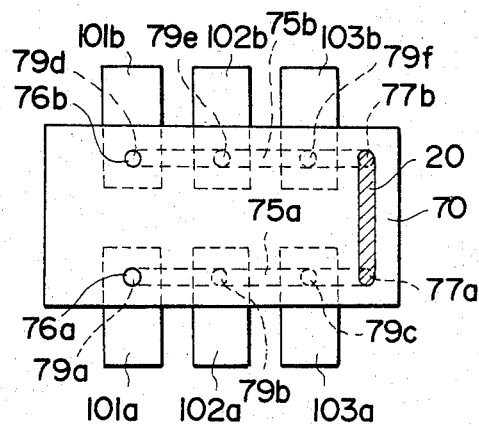
FIG. 7 is a plan view showing another embodiment of the ionic activity measuring device in accordance with the present invention.
Figure 8:
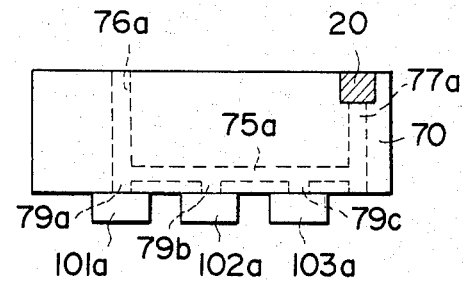
FIG. 8 is a side view of the embodiment shown in FIG. 7.

FIGS. 7 and 8 show another embodiment of the ionic activity measuring device in accordance with the present invention. In this embodiment, the bridge 20 is positioned at the upper section of the substrate 70 near one end thereof, and a pair of air discharging holes 77a and 77b are formed as part of the communication cavities 75a and 75b, respectively, for transporting the liquids introduced from the liquid introducing holes 76a and 76b up to the bridge 20. This configuration is possible since the bridge 20 is constituted of a porous member or a simple groove.

As shown in FIG. 9, in order to easily and certainly inject the liquids into the liquid introducing holes 76a and 76b, it is preferable that adapters 78 for receiving the liquid supply port of a liquid introducing means, for example, a pipette, in airtight relation thereto are formed on the substrate 70 and are annular projections above the surface thereof.

Figure 10:
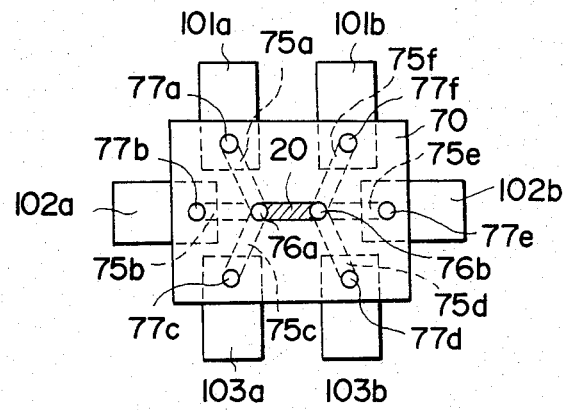
FIG. 10 is a plan view showing a further embodiment of the device in accordance with the present invention.

FIG. 10 is a plan view showing a further embodiment of the ionic activity measuring device in accordance with the present invention. In FIG. 10, the bridge 20 is positioned at the center of the substrate 70. Communication cavities 75a, 75b and 75c radially extending from an end of the bridge 20 to electrodes 101a, 102a and 103a, respectively. Similarly, communication cavities 75d, 75e and 75f radially extend from the other end of the bridge 20 to electrodes 101b, 102b and 103b. The liquid introducing holes 76a and 75b, and air discharging holes 77a, 77b 77c, 77d, 77e and 77f are positioned in the same way as shown in FIGS. 5 and 6.

Figure 11:
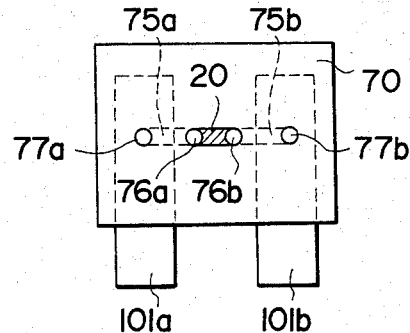
FIG. 11 is a plan view showing a still further embodiment of the ionic activity measuring device in accordance with the present invention, which is provided with a pair of electrodes.

FIG. 11 is a plan view showing a still further embodiment of the ionic activity measuring device in accordance with the present invention, which is provided with a pair of electrodes 101a and 101b for measuring the activity of a single ion. The configuration shown in FIG. 11 is possible since the length of the bridge 20 can be shortened as desired by using the communication cavities 75a and 75b. By shortening the length of the bridge 20, it becomes possible to reduce the amounts of the standard solution and the sample solution used, prevent the liquid composition concentration from changing in the bridge 20, and reduce the time required for the measurement to be conducted after the standard solution and the sample solution are injected into the liquid introducing holes 76a and 76b. The length of the bridge 20 can be shortened as desired also in the embodiments shown in FIGS. 5 to 8 and 10.

It should be noted that the liquid transporting and distributing device in accordance with the present invention can be applied not only to the ionic activity measuring device, but also to various other applications for transporting and distributing small amounts of liquids. For example, the device can be used for simultaneously conducting many kinds of colorimetric analysis by a single liquid spotting step in a colorimetric analysis apparatus provided with many kinds of test paper sheets or a multi-layer analysis film.

I claim:

1. An ionic activity measuring device comprising:
   (a) a liquid transporting and distributing device comprising an outer surface, at least two independent hollow liquid passages positioned in the interior, at least two independent liquid introducing holes which extend from said outer surface to each of said hollow liquid passages, liquid outlet openings extending from the respective hollow liquid passages to said outer surface, at least one liquid outlet opening being provided for each hollow liquid passage, and air discharging holes extending from respective hollow liquid passages to said outer surface, at least one air discharging hole being provided for each hollow liquid passage;
   (b) solid electrodes which are in contact with said liquid outlet openings and which are provided in a number equal to the number of said liquid outlet openings; and
   (c) at least one bridge extending between said liquid introducing holes, between said hollow liquid passages, or between said liquid outlet openings, wherein each of the sections of said liquid introducing holes intersecting with said outer surface or the vicinities of said sections comprises an annular projection extending above said outer surface which functions as an adapter means for receiving or fitting with a liquid supply port of a liquid introducing means in airtight relation therewith for liquid injection into the liquid introducing holes.

* * * * *